United States Patent
Cappa et al.

(10) Patent No.: US 6,581,482 B2
(45) Date of Patent: Jun. 24, 2003

(54) SAMPLER FOR MELTS

(75) Inventors: Guido Cappa, Houthalen (BE); Guido Neyens, Opoeteren (BE); Johan Knevels, Bree (BE)

(73) Assignee: Heraeus Electro-Nite International N.V., Houthalen (BE)

( * ) Notice: Subject to any disclaimer, the term of this patent is extended or adjusted under 35 U.S.C. 154(b) by 0 days.

(21) Appl. No.: 09/788,224

(22) Filed: Feb. 16, 2001

(65) Prior Publication Data

US 2001/0020397 A1 Sep. 13, 2001

(30) Foreign Application Priority Data

Feb. 18, 2000 (DE) .................................. 100 07 494
Sep. 28, 2000 (DE) .................................. 100 49 253

(51) Int. Cl.[7] ................................................ G01N 1/12
(52) U.S. Cl. ................. 73/864.55; 73/864.53; 73/864.59; 73/DIG. 9
(58) Field of Search ................... 73/864.58, 864.53, 73/864.54, 864.59, 864.73, DIG. 9, 864.55

(56) References Cited

U.S. PATENT DOCUMENTS 3,717,034 A * 2/1973 Dukelow et al. ........ 73/864.53
3,877,309 A * 4/1975 Hance .................... 73/864.53
4,002,072 A * 1/1977 Collins .................. 73/DIG. 9
4,089,223 A    5/1978 Collins
4,503,716 A    3/1985 Wuensch
4,932,271 A * 6/1990 Haughton ............... 73/864.53
4,941,364 A * 7/1990 Haughton ............... 73/864.53
5,151,243 A    9/1992 Auer et al.
5,537,881 A    7/1996 White
6,370,973 B1 * 4/2002 Wunsch et al. .......... 73/864.53

FOREIGN PATENT DOCUMENTS

| DE | 197 52 743 A1 | 6/1999 |
| JP | 61271452 | 12/1986 |
| SU | 601 595 A | 4/1978 |
| SU | 1411612 A1 | 7/1988 |

* cited by examiner

Primary Examiner—Daniel S. Larkin
Assistant Examiner—Nashmiya Fayyaz
(74) Attorney, Agent, or Firm—Akin, Gump, Strauss, Hauer & Feld, L.L.P.

(57) ABSTRACT

A sampler is provided for melts, especially for slag lying on top of molten metals, having a one piece or multi-piece body arranged on a carrier. The body of the sampler has an intake and a sample chamber, wherein the intake has a surface which is at least partially formed by a slag-repellant material.

19 Claims, 4 Drawing Sheets

SAMPLER FOR MELTS

BACKGROUND OF THE INVENTION

The invention relates to a sampler for melts, especially for slag lying on a molten metal, having a one piece or multi-piece body arranged on a carrier. The body has an intake and a sample chamber.

Such samplers are known, for example, from published patent applications JP 61-271452 or DE 197 52 743 A1. These slag samplers use the relatively lower density of slag relative to steel or iron melts in order to obtain neat samples. When the slag rises through the intake into the sample chamber, it can lead to an adherence of the slag on the sample chamber walls, with the consequence that the intake of slag into the sample chamber is disturbed or, in extreme cases, even prevented.

SUMMARY OF THE INVENTION

Proceeding from this prior art, an objective underlying the present invention is to improve the known samplers and make possible a high-grade sampling. The objective is accomplished for a sampler of the type described above wherein the intake has a surface which is formed at least partially by a slag-repellant material With the slag-repellant material of the surface of the intake, an adherence of the slag in the intake and, in an extreme case, a blocking of the intake with slag is prevented. Surfaces which have carbon or graphite are especially satisfactory, wherein the graphite or the carbon is preferably uniformly distributed over the entire surface.

It is expedient to form the surface as a graphite layer or to construct it of cardboard or paper. Other materials, such as oil or slaked lime, can also be satisfactory. It is further advantageous to apply an (optionally additional) coating of Teflon® (polytetrafluoroethylene) to the surface. In particular, the part of the body having the intake can be constructed wholly or partially of the slag-repellant material.

In an advantageous embodiment of the invention, the intake is constructed cone-shaped, wherein the end with the smaller cross section is arranged on the sample chamber. Preferably the intake is arranged at least partially beneath the sample chamber in the immersion direction. In an advantageous embodiment of the invention, the sample chamber is constructed cylindrically, and the base surface of the sample chamber has an approximately circular cross section, whose diameter is greater than the thickness (height) of the sample chamber. The intake advantageously opens approximately centrally into the base surface of the sample chamber, which preferably has an annular lateral metal wall. In particular, the sample chamber can have metal walls on all sides.

It is advantageous herein that the opening in the sample chamber or in the metal wall of the sample chamber, through which the slag runs into the sample chamber, have the same size and shape as the end of the conical intake, so that a discontinuity at the opening of the sample chamber is avoided. The opening/mouth of the intake into the sample chamber preferably has a diameter of about 3 to 7 mm, in particular about 5 mm, in order to ensure an optimal intake of the slag into the sample chamber, and in order to prevent slag from flowing out of the sample chamber when raising the sampler after the sampling. It can be advantageous to construct the annular lateral wall thinner than the metal wall of the base surface of the sample chamber.

It has proven to be expedient that the annular lateral metal wall have recesses on its end face directed away from the mouth of the intake. These recesses can be formed in various shapes, for example saw toothed, triangular or rounded off. They make possible a gas passage, that is a gas venting from the sample chamber, in order to make room for the in-flowing molten metal. The lateral metal wall lies against a base surface of the sample chamber such that the gases can escape from the sample chamber through the recesses between the base surface and the lateral metal wall. For this purpose, it is advantageous that the recesses are distributed uniformly over the end face.

On the end face of the lateral metal wall facing away from the opening of the intake into the sample chamber, a cover can lie arranged as an appropriate base surface of the sample chamber, which is advantageously constructed of metal. It is of particular advantage for the cover to have an annular edge bent toward the lateral metal wall and which lies on the lateral metal wall. The cover thereby forms a sort of hollow space, so that the sample forming in the sample chamber projects beyond the end face of the lateral metal wall after removal from the sampler. This wall can then be used as an analysis surface, since it is also formed by the base surface or the cover. The lack of such a projection can lead to this analysis surface receding into the interior of the sample chamber, for example due to shrinkage, so that a measuring head of a measuring device or analysis device does not lie on the sample itself, but rather on the lateral metal wall, so that a correct measurement cannot be performed. The edge preferably projects about 0.5 to 2 mm from the main cover surface.

For ease of sampling, it is advantageous for the body to have an annular notch or groove on its exterior, which preferably tapers to a point at its bottom. A sort of predetermined breaking point is thereby created, at which the body can be destroyed following sampling, so that an easy sample removal is possible. For this purpose, it is particularly expedient that the notch is arranged running around the sample chamber or around the intake, in particular running around the mouth of the intake into the sample chamber.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Figure 1:
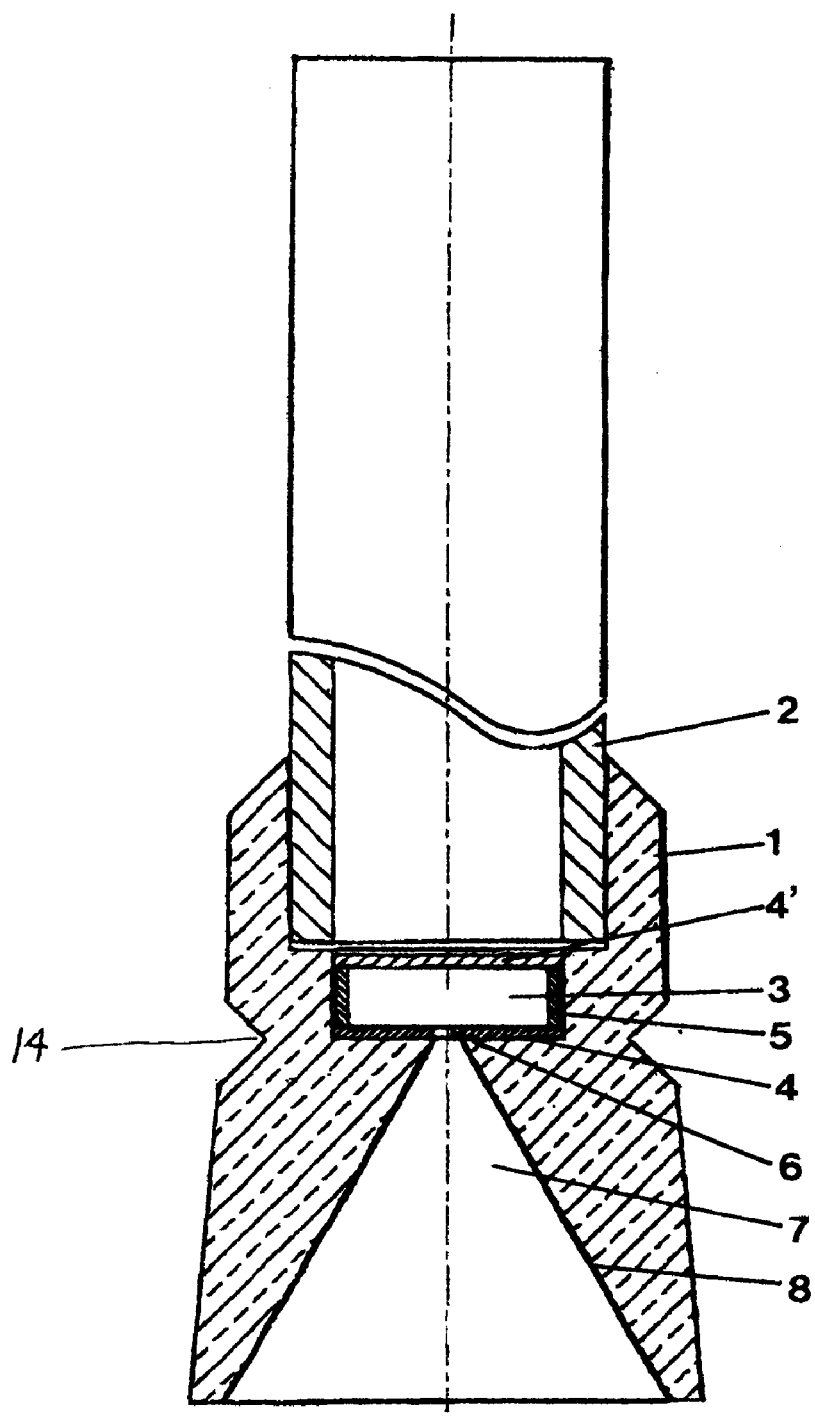
FIG. 1 is a truncated side view, partially in section, of a sampler of the invention.

A sample chamber 3 is arranged in a refractory body 1, for example made of foundry sand, which is mounted on the end of a cardboard tube 2 as a carrier. The sample chamber 3 is arranged approximately axial symmetrically in the refractory body 1. It is constructed substantially cylindrically, wherein the height of the cylinder is substantially smaller than its diameter. The walls of the sample chamber 3 are lined with metal. Here, the metal walls of the base surfaces 4; 4' (steel plates) are thicker than the annular lateral metal wall 5 as a liner surface of steel. This liner is approximately half as thick as the metal walls of the base surfaces 4; 4'. The base surface 4 facing the immersion end of the sample chamber 3 has an opening 6 with a diameter of about 5 mm, which is arranged centrally and to which the intake 7 connects continuously with the same diameter. The intake 7 is constructed cone-shaped. Its walls are lined with a coating 8 of graphite.

Upon immersion of the sampler into the slag layer, the slag first reaches into the intake 7. Due to the conical course, it is assured that only slag gets into the substantially smaller volume of the sample chamber 3 (at most about 30 to 50%) in relation to the volume of the intake 7. The slag lying on the melt is gathered over a large surface, so that even with a smaller thickness of the slag layer, sufficient slag is taken up for filling the sample chamber with slag. The conical shape assures a uniform and continuous narrowing of the intake 7, wherein an adherence of the slag to the wall is prevented by the coating 8. The refractory body 1 has an annular groove or notch 14 in its exterior wall. The notch 14 is at about the same level where in the intake 7 meets the sample chamber 3, and serves as a score line, so that the body can be easily broken open after the sampling. The samples obtained with the device of the invention are thus directly available for an analysis.

Figure 2:
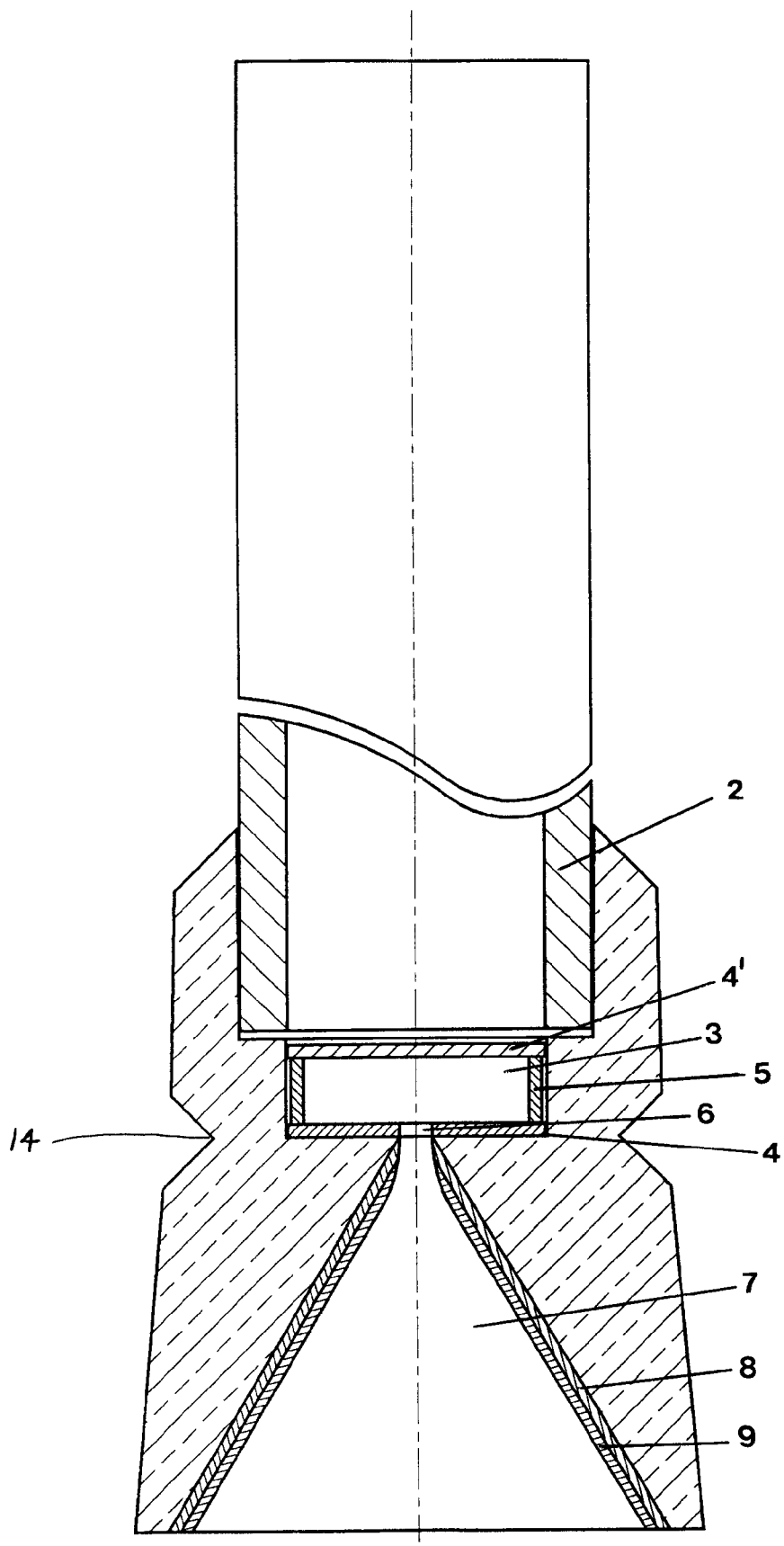
FIG. 2 is a similar view as in FIG. 1 of a further embodiment of a sampler of the invention.
Figure 3:
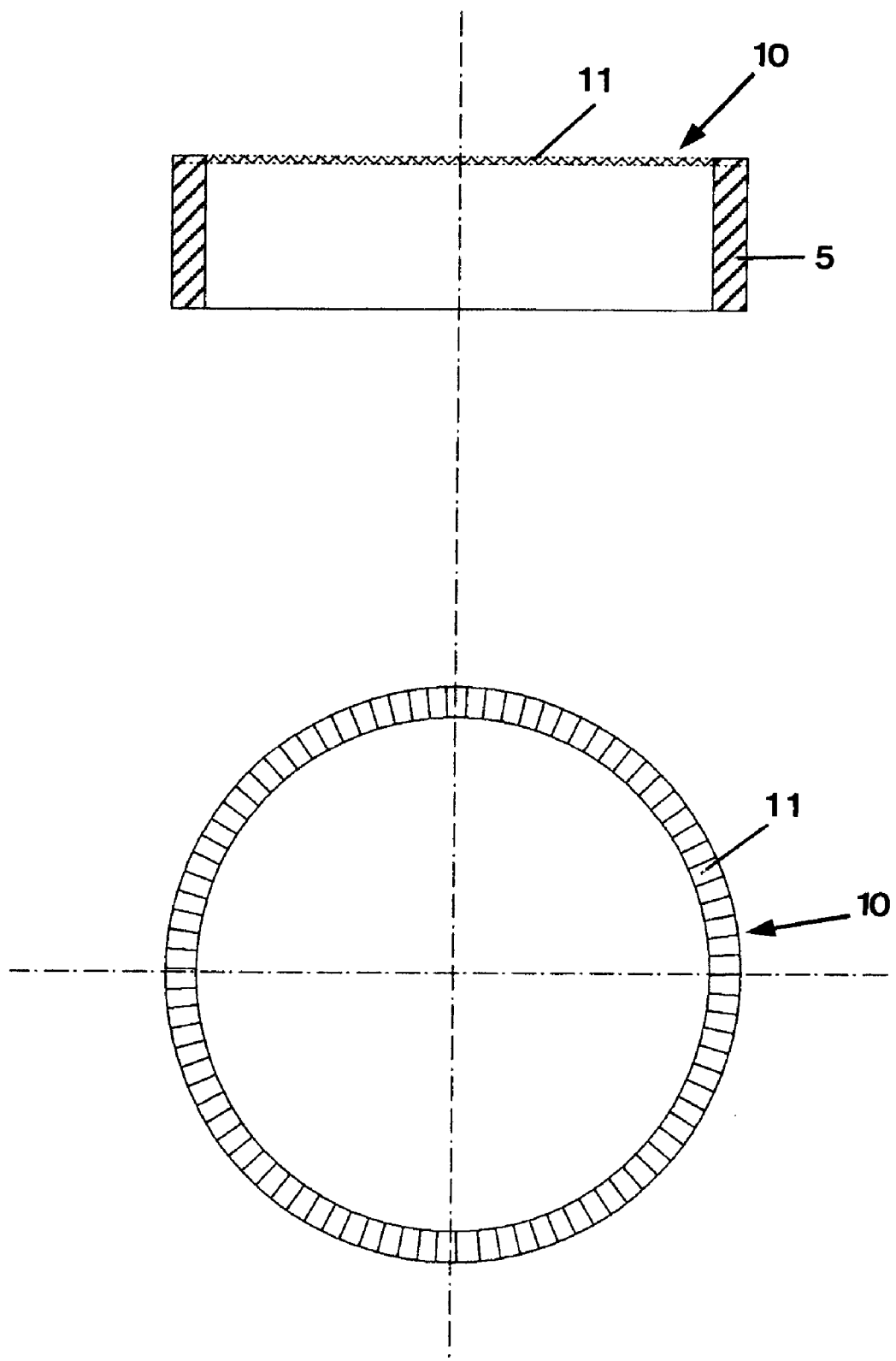
FIG. 3 is a side sectional view and a plan view of a construction of the lateral metal wall of a sample chamber of a sampler of the invention.
Figure 4:
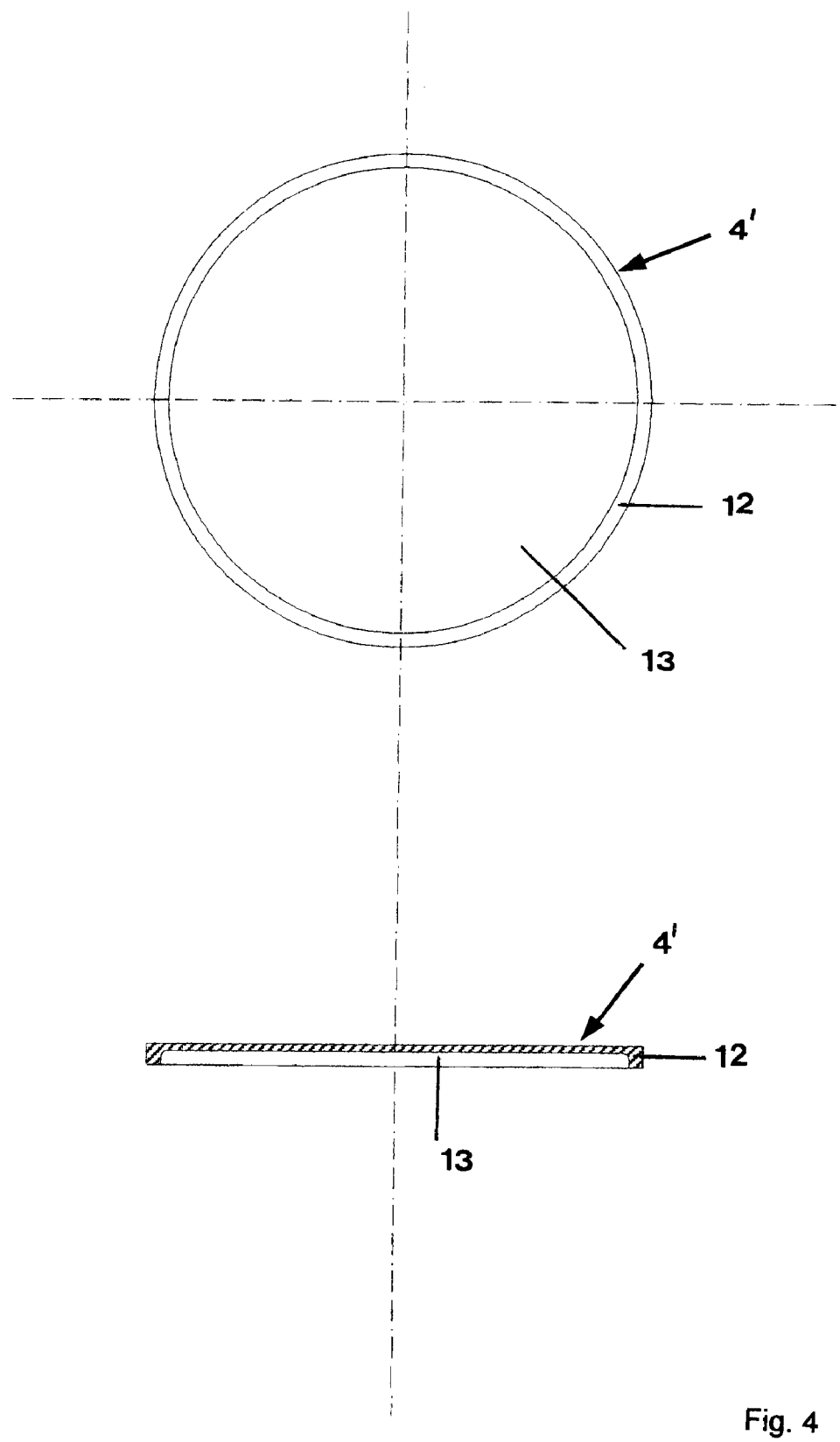
FIG. 4 is a bottom plan view and a side sectional view of a construction of the cover for a sample chamber of a sampler of the invention.

FIG. 2 depicts a sampler similar to FIG. 1, wherein in addition a Teflon® layer 9 is applied to the coating 8. In FIG. 3, the lateral metal wall 5 is represented, whose one end face 10 has notches 11, arranged annularly and sequentially one after another, which have the shape of triangles. FIG. 4 shows a base surface 4' constructed as a cover, which has an edge 12. The edge 12 is designed for installation on the end face 10 of the metal wall. The edge 12 projects about 1 mm from the cover surface 13.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:
1. A sampler for melts comprising a one piece or multi-piece body (1) arranged on a the body (1) having an intake (7) and a cylindrical sample chamber (3) with circular cross section first and second base surfaces (4; 4') and a diameter which is greater than a height of the sample chamber (3), wherein the intake (7) has a surface (8) which is formed at least partially of a slag-repellent material and opens approximately centrally into an opening (6) in the first base surface (4) of the sample chamber (3), and wherein the sample chamber (3) has at least one annular lateral metal wall (5) having recesses (11) on a wall end face (10) directed away from the opening (6) to the intake (7).

2. The sampler according to claim 1, wherein the intake surface (8) comprises carbon.

3. The sampler according to claim 2, wherein the intake surface (8) comprises a layer selected from the group consisting of graphite, cardboard and paper.

4. The sampler according to claim 1, wherein the intake surface (8) has a coating of polytetrafluoroethylene.

5. The sampler according to claim 1, wherein a part of the body (1) having the intake (7) is formed at least partially of slag-repellent material.

6. The sampler according to claim 1, wherein the intake (7) is cone-shaped and wherein an end of the intake (7) with a smaller cross section is arranged at the sample chamber (3).

7. The sampler according to claim 1, wherein the intake (7) is arranged at least partially beneath the sample chamber (3) in an immersion direction of the sampler.

8. The sampler according to claim 1, wherein the sample chamber (3) has metal walls on all sides.

9. The sampler according to claim 8, wherein the annular lateral metal wall (5) is thinner than metal walls of the base surfaces (4; 4') of the sample chamber (3).

10. The sampler according to claim 1, wherein the recesses (11) are distributed uniformly over the end face (10).

11. The sampler according to claim 1, wherein the second base surface (4') lying on the end face (10) comprises a cover.

12. The sampler according to claim 11, wherein the cover is made of metal.

13. The sampler according to claim 11, wherein the cover has an annular edge (12) bent toward the lateral metal wall (5), which edge (12) lies on the lateral metal wall (5).

14. The sampler according to claim 13, wherein the edge (12) projects about 0.5 to 2 mm from a surface (13) of the cover.

15. The sampler according to claim 1, wherein the body (1) has an annular notch (14) on an exterior portion of the body (1).

16. The sampler according to claim 15, wherein the notch (14) is arranged running around the sample chamber (3).

17. The sampler according to claim 15, wherein the notch is arranged running around an opening (6) of the sample chamber (3) from the intake (7).

18. The sampler according to claim 1, wherein an opening (6) in the sample chamber (3) from the intake (7) has a diameter of about 3 to 7 mm.

19. The sampler according to claim 1, wherein the melts comprise slag lying on a molten metal.

\* \* \* \* \*